(12) United States Patent
Bonrath et al.

(10) Patent No.: US 9,101,917 B2
(45) Date of Patent: Aug. 11, 2015

(54) STRUCTURED CATALYST

(75) Inventors: Werner Bonrath, Basel (CH); Lioubov Kiwi-Minsker, Basel (CH); Igor Iouranov, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 376 days.

(21) Appl. No.: 13/807,972

(22) PCT Filed: Jul. 1, 2011

(86) PCT No.: PCT/EP2011/061159
§ 371 (c)(1),
(2), (4) Date: Mar. 18, 2013

(87) PCT Pub. No.: WO2012/001166
PCT Pub. Date: Jan. 5, 2012

(65) Prior Publication Data
US 2013/0217923 A1    Aug. 22, 2013

(30) Foreign Application Priority Data

Jul. 1, 2010    (CH) ........................................ 1079/10

(51) Int. Cl.
| | | |
|---|---|---|
| *C07C 29/17* | (2006.01) | |
| *B01J 23/89* | (2006.01) | |
| *B01J 23/44* | (2006.01) | |
| *B01J 23/60* | (2006.01) | |
| *B01J 35/00* | (2006.01) | |
| *B01J 35/06* | (2006.01) | |
| *B01J 37/02* | (2006.01) | |
| *B01J 37/08* | (2006.01) | |
| *B01J 37/18* | (2006.01) | |
| *B01J 23/58* | (2006.01) | |
| *B01J 23/652* | (2006.01) | |
| *B01J 23/656* | (2006.01) | |

(52) U.S. Cl.
CPC .............. *B01J 23/8993* (2013.01); *B01J 23/44* (2013.01); *B01J 23/60* (2013.01); *B01J 35/006* (2013.01); *B01J 35/06* (2013.01); *B01J 37/0217* (2013.01); *B01J 37/0225* (2013.01); *B01J 37/0242* (2013.01); *B01J 37/0244* (2013.01); *B01J 37/08* (2013.01); *B01J 37/18* (2013.10); *C07C 29/17* (2013.01); *B01J 23/58* (2013.01); *B01J 23/6522* (2013.01); *B01J 23/6562* (2013.01)

(58) Field of Classification Search
CPC ........ B01J 23/8993; B01J 23/44; B01J 23/60; C07C 29/17
USPC .......... 502/330, 326, 226, 329; 568/875, 903, 568/803, 909.5
See application file for complete search history.

(56) References Cited

U.S. PATENT DOCUMENTS

| | | |
|---|---|---|
| 5,063,194 A | 11/1991 | Broecker et al. |
| 2001/0039368 A1 | 11/2001 | Reimer et al. |
| 2011/0237841 A1 | 9/2011 | Bonrath et al. |

FOREIGN PATENT DOCUMENTS

| | | |
|---|---|---|
| CN | 101616733 | 12/2009 |
| WO | WO 2008/101603 | 8/2008 |

OTHER PUBLICATIONS

International Search Report for PCT/EP2011/061159, mailed Oct. 11, 2011.
CN Office Action dated May 7, 2015.

*Primary Examiner* — Elvis O Price
(74) *Attorney, Agent, or Firm* — Nixon & Vanderhye P.C.

(57) ABSTRACT

The present invention relates to novel structured catalysts based on sintered metal fibers (SMF) coated by a basic oxide layer with Pd-nanoparticles, to reactions of organic compounds with hydrogen in the presence of said catalyst and an organic base as well as to vitamins, carotinoids, perfume ingredients, and/or food or feed ingredients prepared by using this reaction.

21 Claims, No Drawings

STRUCTURED CATALYST

This application is the U.S. national phase of International Application No. PCT/EP2011/061159 filed 1 Jul. 2011 which designated the U.S. and claims priority to CH Patent Application No. 1079/10 filed 1 Jul. 2010, the entire contents of each of which are hereby incorporated by reference.

The present invention relates to novel structured catalysts based on sintered metal fibers (SMF) coated by a basic oxide layer with Pd-nanoparticles, to reactions of organic compounds with hydrogen in the presence of said catalyst and an organic base as well as to vitamins, carotenoids, perfume ingredients, and/or food or feed ingredients prepared by using this reaction.

Selective catalytic hydrogenations of alkynols to alkenols are important processes in the fine chemicals industry. Pd-based catalysts are known to give the highest selectivity and yield. Preferential formation of olefinic alcohols is attributed to the stronger adsorption of acetylenic alcohols in comparison with the half-hydrogenation product. Catalytic performance of palladium is known to be strongly influenced by its dispersion, nature of support and the use of promoters and additives. Catalyst design taking into consideration these factors can allow a yield increase of target product and catalyst reuse.

In general, Pd atoms of low coordination number present in small particles of 1-2 nm provide too strong alkynol adsorption diminishing turnover frequency and selectivity. This phenomenon is known as a geometric or "ensemble" effect. Particles of 7 to 10 nm size demonstrate better catalytic performance in hydrogenations of 2-butyne-1,4-diol and 2-methyl-3-butyn-2-ol (MBY) as compared to highly dispersed Pd.

In industry hydrogenations as describes above are usually carried out in stirred tank reactors with Lindlar catalyst, (5% Pd/CaCO$_3$ modified by lead acetate) and often with addition of quinoline. Lindlar catalyst being a fine powder is difficult to handle and requires filtration after the reaction. In this respect, structured catalysts are beneficial for process intensification and safety. Monoliths, membranes, metallic grids, bidimensional glass and carbon fibers were used as catalyst supports in liquid-phase hydrogenations. Monoliths showed similar selectivity but much lower activity per Pd loading in comparison with a slurry catalyst in 3-methyl-1-pentyn-3-ol and 2-butyne-1,4-diol hydrogenations. The use of highly-selective bimetallic Pd—Ru (9:1) H$_2$-permeable membrane in 2-methyl-3-butyn-2-ol hydrogenation is limited by the high content of noble metal and low productivity per gram of Pd. Metallic grids have a disadvantage of low geometric surface area of ~100 cm$^2$/g. Fabrics of activated carbon fibers used in 2-butyne-1,4-diol hydrogenation possess low mechanical strength.

The production of the structured metal-based catalysts known from the prior art needs relatively harsh reaction conditions. The alloys used for such catalytic systems usually contain aluminum and have to be heated to over 1000° C. for several hours. Furthermore, non aqueous organic solvents and stabilizers, such acetoin and/or monoethanolamine are used for coating of the alloy surface.

The goal of the present invention was to find a structured catalyst, which has comparable catalytic properties than those known from the prior art, but is easy to handle and separate from the reaction mixture for an eventual reuse and which can be produced by using lower temperature and avoiding solvents, which are not eco-friendly.

It was surprisingly found that a structured catalyst based on sintered metal fibers coated by a basic oxide layer (preferably comprising ZnO or ZnO and Al$_2$O$_3$) impregnated with Pd-nanoparticles and wherein the alloy is free from Al overcomes the above mentioned disadvantages.

Therefore, the present invention relates to a structured catalyst based on sintered metal fibers (SMF) coated by a basic oxide layer impregnated with Pd-nanoparticles, characterized in that the SMF contains an alloy wherein the alloy is free from Al.

Preferably the basic oxide layer comprises ZnO or ZnO and Al$_2$O$_3$.

Three-dimensional sintered metal fibers (SMF) consisting of metallic microfibers were chosen as a structured catalyst support. SMF have high thermal conductivity that is a great advantage in exothermic hydrogenations, high porosity and permeability. The metal fiber matrix also acts as a micron-scale static mixer eliminating channeling. In addition, high mechanical strength and chemical and thermal stability, easy shaping make SMF suitable support materials when developing catalyst aiming on intensification of catalytic hydrogenation.

By the expression "free from aluminum" it is meant that the alloy could contain traces of aluminum (Al). Al is not added to the alloy intentionally. The content of Al is less that 0.1% by weight (wt.-%, based on the total weight of the alloy).

SMF coated with a thin layer of ZnO are known as efficient support for 2-methyl-3-butyn-2-ol hydrogenation. Pd nanoparticles were deposited from the before-hand prepared sol, and the material was heated in hydrogen atmosphere to create Pd$_y$Zn$_x$ phase. ZnO layer acts both as a basic support and a Pd promoter. The Pd/ZnO/SMF material was tested for mechanical stability, and its catalytic behavior was studied in MBY hydrogenation.

It is also possible to coat the SMF by a mixture of ZnO and Al$_2$O$_3$ and optionally with one or more other metal oxide. Such other metal oxide can be for example MgO, MnO, Cr$_2$O$_3$, CuO and Fe$_2$O$_3$.

The term "structured catalyst" as used herein refers to catalysts wherein the spatial organization of the catalyst is controlled. Structured catalysts are known in the art, see, e.g., *Chimia* 56(4), 2002, 159-163. Examples of structured catalysts are ceramic carrier constructions (honeycombs) and fibrous structures, especially filamentous (woven or not) materials. Preferably metal fiber materials, which are free from Al are used for the catalysts of the present invention. The individual fibers of these materials preferably have a diameter of about 2 µm to about 100 µm, especially a diameter of no more than about 20 µm. The materials may be chemically treated to modify the specific surface area and/or may have a coating, e.g. of metal oxides such as Al, Ti, Mg, Zn, etc.

In a preferred embodiment of the present invention the SMF consists of stainless steel, which optionally can be pre-oxidized.

In the context of the present invention the term "stainless steel" is in accordance with the standard norm defined in EN 10088:2005. Stainless steel comprises at least 10.5 wt.-% of chromium (Cr). The content can be up to 26 wt.-%. Some types of stainless steel also comprise Ni, Mn, C, Mo, Ti and/or Nb.

In a further embodiment of the present invention the Pd-nanoparticles are Pd$^0$-nanoparticles.

A further embodiment of the present invention relates to a structured catalyst, wherein a portion of the Pd-nanoparticles are within Pd$_y$M$_x$ phase, wherein M is Zn or Zn and Al and optionally Cr, Mn, Co and/or Mg, and wherein the Pd$_y$M$_x$ phase is preferably formed through thermal activation in a hydrogen atmosphere.

Usually the Pd-nanoparticles have a size between 0.5 and 100 nm, preferably between 2 and 20, more preferably between 2 and 15 nm, especially preferred between 5 and 12 nm and most preferably between 7 and 10 nm. It is also possible that the ZnO layer is a grain-structured ZnO layer.

The catalyst comprises usually between 0.001 and 5 wt.-% of Pd nanoparticles, preferably between 0.01 and 2 wt.-%, more preferably between 0.05 and 1 wt.-% and most preferably between 0.1 and 0.3 wt.-% based on the weight of the catalyst.

The present invention further relates to a structured catalyst as defined above, wherein the catalyst is containing between 0.01 and 20 wt.-% of ZnO and/or MgO (or a mixture of oxides, such as $Al_2O_3$, MnO, $Cr_2O_3$, CuO and $Fe_2O_3$), preferably between 0.1 and 10 wt.-%, more preferably between 1.5 and 10 wt.-% and most preferably between 2 and 8 wt.-%, based on the total weight of the catalyst.

The production of the structured catalyst usually comprises the following steps:

1) pre-treatment (cleaning and calcination) of the alloy support
2) coating of the alloy support by a metal oxide
3) synthesis and deposition of the Pd nanoparticles on the coated alloy support
4) post-treatment of the catalyst.

Step 1) is usually done to remove all contamination from the alloy surface. Any suitable method for that purpose can be used. A suitable method is the treatment of the alloy with boiling toluene for at least 30 minutes. The alloy is then dried. The alloy, which is used in the present invention is then oxidized in air at a temperature of less than 600° C. Usually this step is done at a temperature of around 450° C. (The prior art alloys usually need temperature of more than 1000° C.!).

Therefore a further embodiment of the present invention is a process for the production of structured catalysts as defined above, wherein in the pre-treatment, the reaction (treatment) temperature is less than 600° C., preferably around 450° C.

Step 2) is then is carried out in water. The coating precursor of is dissolved in water. Usually the alloy is dipped into that solution, followed by a drying step and the at least one calcincation step. Therefore a further embodiment of the present invention is a process for the production of structured catalysts as defined above, wherein in the coating step, water is used as the solvent.

Step 3) is done according to well known methods. Usually a suitable Pd salt (such as i.e. $PdCl_2$) is dissolved together with stabilizing agent (such for i.e. $Na_2MoO_4.H_2O$) and reduced by $H_2$ giving a stable Pd sol. The obtained Pd sol is diluted with water and the treated alloy from step 1) and step 2) is put into such a solution for a certain time. The so treated alloy is then dried. Step 4) is carried out according to well known methods. Usually the material obtained from step 3) is treated in a gaseous flow containing hydrogen at 300° C.

The structured catalyst according to the present invention is used in hydrogenation processes of organic material. Therefore the present invention also relates to a process of reacting an organic starting material with hydrogen in the presence of the catalyst as defined above.

Preferably the organic starting material in these reactions comprises a carbon-carbon triple bond. More preferably the organic starting material is an alkynol. Especially preferred organic starting materials are compounds of formula (I),

wherein
$R_1$ is H, a linear or branched $C_5$-$C_{35}$ alkyl moiety or a linear or branched $C_5$-$C_{35}$ alkenyl moiety, wherein the C chain can be substituted, and
$R_2$ is linear or branched $C_1$-$C_4$ alkyl, wherein the C chain can be substituted.

Preferred compounds of formula (I) are those wherein
$R_1$ is H, a linear or branched $C_5$-$C_{30}$ alkyl moiety or a linear or branched $C_5$-$C_{30}$ alkenyl moiety, wherein the C chain can be substituted, and
$R_2$ is a linear or branched $C_1$-$C_4$ alkyl moiety, wherein the C chain can be substituted.

More preferred compounds of formula (I) are those wherein
$R_1$ is H, a linear or branched $C_6$-$C_{16}$ alkyl moiety or a linear or branched $C_6$-$C_{16}$ alkenyl moiety, wherein the C chain can be substituted, and
$R_2$ is a $C_1$-$C_2$ alkyl moiety, wherein the C chain can be substituted.

Most preferred compounds of formula (I) are those wherein
$R_1$ is a linear or branched $C_6$-, $C_{11}$- or $C_{16}$-alkyl moiety or a linear or branched $C_6$-, $C_{11}$- or $C_{16}$-alkenyl moiety, and
$R_2$ is a $C_1$-$C_2$ alkyl moiety.

Examples of especially preferred compounds, which are used in a process as disclosed above are 2-methyl-3-butyn-2-ol (MBY) and dehydroisophytol (DIP).

The hydrogenation in accordance with the present invention can be carried out under conditions conventionally used for hydrogenations.

The process according to the present invention, wherein the structured catalyst as defined above is used, is usually carried out at a pressure between 1.1 and 30 bar, preferably between 1.1 and 15 bar, more preferably between 1.5 and 10 bar and most preferably between 2 and 8 bar.

The process according to the present invention, wherein the structured catalyst as defined above is used, is carried out at reaction temperature between 250 K and 420 K, preferably between 273 K and 380 K, more preferably between 274 K and 350 K and most preferably between 295 K and 330 K.

The process according to the present invention, wherein the structured catalyst as defined above is used, can further comprise the addition of at least one organic base to the reaction, preferably 3,6-dithia-1,8-octandiol, thiophene, dipropyl sulfide, tetrahydrothiophene, quinoline, pyridine and diethylaminoethanol. In case such bases are used, the base(s) and the Pd have a ratio of between 1:1 and 500:1, preferably between 2:1 and 150:1 more preferably between 5:1 and 50:1 and most preferably between 10:1 and 30:1.

The process according to the present invention, wherein the structured catalyst as defined above is used, wherein the organic starting material is reacting with hydrogen is carried out in the presence of the catalyst as defined above and optionally in the presence of a solvent, wherein the solvent is preferably water.

The process according to the present invention, wherein the structured catalyst as defined above is used, usually further comprises separation of the catalyst after the reaction and exposing the used catalyst to ultrasonic radiation, preferably in a vessel containing alcohol, such as for example ethanol.

The reaction product, which is obtained by a process according to the present invention, wherein the structured catalyst as defined above is used is preferably as an intermediate of a vitamin, a carotinoid, a perfume ingredient, and/or a food ingredient.

The following Examples illustrate the invention further without limiting it. All percentages and parts, which are given, are related to the weight and the temperatures are given in K or in ° C., when not otherwise stated.

EXAMPLES

Materials

Sintered Metal Fibers ($SMF_{SS}$), stainless steel 316L, 40FP3 (available from Southwest Screen & Filters SA (now Bekaert SA, Belgium))

Example 1

0.19% Pd/5% ($Al_2O_3$+ZnO)/$SMF_{SS}$

Step 1): Pre-Treatment

In order to remove contaminations, $SMF_{SS}$ panels (10×10 cm, m=6-7 g) were treated in boiling toluene for 0.5 hour and air-dried. $SMF_{SS}$ was then oxidized in air at 450° C. for 3 hours. After cooling down to room temperature, treated $SMF_{SS}$ was stored in a dry atmosphere.

Step 2): Support Coating with Mixed Oxide

The $SMF_{SS}$ panels cleaned as described in step 1) were dip-coated by ZnO+$Al_2O_3$ (Zn:Al ratio=1:1) layer. A ZnO+$Al_2O_3$ precursor solution was prepared as following: 200 g of $Al(NO_3)_3.9H_2O$ were dissolved in 700 ml of distilled water. The solution was heated up to 95° C. 43.4 g of ZnO were added to the solution. Heating and stirring were maintained until ZnO was completely dissolved. The solution was then cooled down to room temperature. ZnO+$Al_2O_3$ (Zn:Al ratio=1:1) layer deposition was performed by dipping $SMF_{SS}$ panels into the ZnO+$Al_2O_3$ precursor solution followed by drying in air at room temperature (1 hour) and calcination at 450° C. (1 hour, temperature ramp—2° C./min). The dipping-drying-calcination cycle was repeated 2 times to deposit ~5 wt.-% of ZnO+$Al_2O_3$ (Zn:Al ratio=1:1). The prepared 5% (ZnO+$Al_2O_3$)/$SMF_{SS}$ was stored in a dry atmosphere.

Step 3): Synthesis of Pd Nanoparticles and the Deposition of the Pd Nanoparticles Pd nanoparticles solution was prepared as following: 0.121 g of $Na_2MoO_4.H_2O$ and 0.088 g of $PdCl_2$ were dissolved in 20 ml of deionized water under heating (90-95° C.) and stirring (magnet bar). Heating and stirring are continued until complete evaporation of water in order to dissolve completely $PdCl_2$. The evaporation-dissolving cycle was repeated two times. Finally, 50 ml of deionized water were added to dissolve the residue. Pd sol was formed by bubbling hydrogen (250 ml/min) for 1 hour through the filtrated Pd precursor solution at room temperature. In doing so, the solution color turned from brown to black.

50 ml of the so obtained Pd sol were diluted by deionized water up to 4 l in a beaker. The obtained solution was black and opaque. The coated $SMF_{SS}$ panel as prepared in step 1) and 2) is immersed completely into the sol and kept under stirring (magnetic bar) for 2 hours. In order to provide homogeneity of Pd nanoparticle deposition, the panels were turned every 15 min for 180° C. During the process, the solution became almost transparent and colorless. The color of the SMF panels turned to deep grey. After Pd deposition the catalysts were rinsed with water and dried at ambient conditions for 1 hour. The resulting Pd content was found to be 0.19 wt.-%. The prepared materials were stored in a dry atmosphere.

Step 4): Post-Treatment

The so produced catalyst was subjected to a temperature reductive treatment (300° C.; temperature ramp—10° C./min) in $H_2$—Ar atmosphere (ratio—1:9; total flow rate—450 ml/min) for 2 hours. After cooling down under the $H_2$—Ar flow, the catalysts were stored in a dry atmosphere.

Example 2

0.2% Pd/5% (ZnO+MgO+$Al_2O_3$)/$SMF_{SS}$

All steps are carried out in analogy to Example 1 except step 2).

The support coating was done by using a different coating system. The $SMF_{SS}$ was dip-coated by ZnO+MgO+$Al_2O_3$ (Zn:Mg:Al molar ratio 1:1:2)-layer. The ZnO+MgO+$Al_2O_3$ precursor solution was prepared as following: 200 g of $Al(NO_3)_3.9H_2O$ were dissolved in 700 ml of distilled water. The solution was heated up to 95° C. 11.0 g of MgO and 21.7 g of ZnO were added to the solution. Heating and stirring were maintained until MgO and ZnO were completely dissolved. The solution was then cooled down to room temperature.

ZnO+MgO+$Al_2O_3$ (Zn:Mg:Al molar ratio 1:1:2) layer deposition was performed by dipping $SMF_{SS}$ panels into the ZnO+MgO+$Al_2O_3$ precursor solution followed by drying in air at room temperature (1 hour) and calcination at 450° C. (1 hour, temperature ramp—2° C./min). The dipping-drying-calcination cycle was repeated 2 times to deposit ~5 wt.-% of ZnO+MgO+$Al_2O_3$ (Mg:Al molar ratio 1:1:2). The prepared 5% (ZnO+MgO+$Al_2O_3$)/$SMF_{SS}$ was stored in a dry atmosphere.

Example 3

0.2% Pd/5% (ZnO)/$SMF_{SS}$

All steps are carried out in analogy to Example 1 except step 2). The support coating was done by using a different coating system. The $SMF_{SS}$ was dip-coated by a ZnO-layer.

Example 4

0.2% Pd/5% ($Cr_2O_3$+$Al_2O_3$+ZnO)/$SMF_{SS}$

The steps according to example 1 were repeated, but in the coating step such an amount of $Cr(NO_3)_3$ were added that 10 wt.-% of the oxide layer is $Cr_2O_3$.

Example 5

0.2% Pd/5% (MnO+$Al_2O_3$+ZnO)/$SMF_{SS}$

The steps according to example 1 were repeated, but in the coating step such an amount of $Mn(NO_3)_2$ were added that 10 wt.-% of the oxide layer is MnO.

Example 6

0.2% Pd/5% (CuO+$Al_2O_3$+ZnO)/$SMF_{SS}$

The steps according to example 1 were repeated, but in the coating step such an amount of $Cu(NO_3)_2$ were added that 10 wt.-% of the oxide layer is CuO.

Example 7

Selective DIP hydrogenation

General Remarks

Hydrogenations were carried out in a batch stainless steel reactor (150 or 250 ml autoclave, Buchi AG, Uster, Switzerland) equipped with a heating jacket and a hydrogen supply system. The structured catalyst (0.8-1.6 g) was placed between two metal gauzes (2×4-8.5 cm) fixed on the self-gassing hollow shaft stirrer. Baffles were placed inside the reactor to eliminate vortex formation. The reactor was filled with a substrate and catalyst, flushed with $N_2$. At working temperature the reactor was flushed with hydrogen and pressurized. During the course of the reaction, the pressure in the reactor was maintained constant. The experiments were carried out at 65-80° C. and 4-8 bar $H_2$ pressure at intensive stirring of 1800-2000 rpm. Temperature and pressure were controlled with the help of a Pt-100 temperature sensor and pressure sensor respectively. The hydrogen consumption, reaction temperature, reaction pressure and stirring speed were monitored and recorded continuously throughout the reaction with the help of a computer.

The samples of the reaction mixtures were periodically withdrawn from the reactor via a sampling tube and analyzed by GC.

Product yield was defined as $Y = mol_{substrate}$ (converted into the product)/$mol_{substrate}$ (introduced)·100%, conversion as $X = mol_{substrate}$ (reacted)/$mol_{substrate}$ (introduced)·100%, selectivity to the product as $S = Y/X \sim 100\%$.

Solvent-free selective DIP hydrogenation reactions were carried out in a semi-batch stainless steel reactor (150 ml, Büchi AG) equipped with a heating jacket and a hydrogen supply system. The SMF catalysts were placed between two grids fixed on a self-gassing hollow shaft stirrer. The experiments were carried out at 80° C. and 0.4 MPa $H_2$ pressure under stirring at 1800-2000 rpm. In some experiments, the modifier 2,2'-ethylenedithiodiethanol was added to the reaction mixture ($c_{mod} = 5.9 \cdot 10^{-4} - 1.2 \cdot 10^{-2}$ wt.-%).

TABLE 1

| No. | Catalyst | $m_{cat}$ (g) | Reaction modifier | $R_{ini}$ (mol/mol$_{Pd}$·s) | Selectivity (%) |
|---|---|---|---|---|---|
| 1 | 0.19% Pd/ 5% ($Al_2O_3$ + ZnO)/$SMF_{SS}$ | 0.64 | — | 2.41 | 91.1 (X = 15%) |
| 2 | 0.19% Pd/ 5% ($Al_2O_3$ + ZnO)/$SMF_{SS}$ | 0.64 | 2,2'-ethylenedithiodiethanol, 10 mg | 1.60 | 96.0 (X = 97%) |
| 3 | 0.06% Pd/ 5% $Al_2O_3$ + ZnO)/$SMF_{SS}$ | 0.65 | 2,2'-ethylenedithiodiethanol 10 mg | 3.46 | 95.5 (X = 97%) |
| 4 | 0.2% Pd/ 5% ($Cr_2O_3$ + $Al_2O_3$ + ZnO)/$SMF_{SS}$ | 0.59 | — | 6.49 | 92.2 (X = 70%) |
| 5 | 0.2% Pd/ 5% ($Cr_2O_3$ + $Al_2O_3$ + ZnO)/$SMF_{SS}$ | 0.59 | 2,2'-ethylenedithiodiethanol 10 mg | 1.32 | 97.0 (X = 98%) |
| 6 | 0.2% Pd/ 5% (CuO + $Al_2O_3$ + ZnO)/$SMF_{SS}$ | 0.61 | — | 3.0 | 91.6 (X = 15%) |
| 7 | 0.2% Pd/ 5% (MnO + $Al_2O_3$ + ZnO)/$SMF_{SS}$ | 0.63 | — | 3.05 | 90.7 (X = 15%) |

Example 8

0.2% Pd/5% ZnO/$SMF_{SS}$

The catalytic system of Example 3 was repeated but instead of using $PdCl_2$ $Pd(CH_3COO)_2$ was used.

Table 2. Structured catalysts prepared using $Pd(CH_3COO)_2$ in selective DIP hydrogenation.

TABLE 2

Structured catalysts prepared using $Pd(CH_3COO)_2$ in selective DIP hydrogenation.

| No. | Catalyst | $m_{cat}$ (g) | Reaction modifier | $R_{ini}$ (mol/mol$_{Pd}$·s) | Selectivity (%) |
|---|---|---|---|---|---|
| 8a | 0.15% Pd/ 5% ZnO/$SMF_{SS}$($PdAc_2$) | 0.59 | — | 9.8 | 88.2 (X = 95%) |
| 8b | 0.15% Pd/ 5% ZnO/$SMF_{SS}$($PdAc_2$) | 0.59 | 2,2'-ethylenedithiodiethanol, 12 mg | 4.8 | 94.2 (X = 99%) |
| 8c | 0.15% Pd/ 5% ZnO/$SMF_{SS}$($PdAc_2$) | 0.59 | 2,2'-ethylenedithiodiethanol, 25 mg | 4.1 | 95.5 (X = 95%) |

Example 9

MBY Hydrogenation

Solvent-free selective hydrogenation of 2-methyl-3-butyn-2-ol (MBY) to 2-methyl-3-butene-2-ol (MBE) was carried out in a 250 ml reactor at 65° C. under $H_2$ pressure (4 bar) using 200 ml of MBY and the catalysts (1.0-1.6 g) prepared as described in Example 3.

Example 10

2-butyn-1,4-diol Hydrogenation

Solvent-free selective hydrogenation of 2-butyn-1,4-diol ($B_3D$) to 2-buten-1,4-diol (B2D) was carried out in a 150 ml reactor at 80° C. under $H_2$ pressure (15 bar) using 100 ml of melted $B_3D$ and the catalysts (0.6-1.0 g) prepared as described in Examples 1.

TABLE 3

Performance of the structured catalysts

| No. | $m_{cat}$ (g) | $R_{ini}$ (mol/mol$_{Pd}$ · s) | Selectivity (%) |
|---|---|---|---|
| 9 | 1.53 | 4.55 | 97.3 (x = 97%) |
| 10 | 0.65 | 2.41 | 98.8 (x = 99%) |

The invention claimed is:

1. A structured catalyst comprising sintered metal fibers (SMF) coated by a basic oxide layer impregnated with Pd-nanoparticles, wherein the SMF contain an alloy which is free from Al.

2. The catalyst according to claim 1, wherein the basic oxide layer comprises ZnO or ZnO and $Al_2O_3$.

3. The catalyst according to claim 1, wherein the alloy is stainless steel.

4. The catalyst according to claim 1, wherein the basic oxide layer comprises at least another metal oxide of Cr, Mn, Cu or Mg.

5. The catalyst according to claim 1, wherein the alloy is preoxidized.

6. The catalyst of claim 1, wherein the Pd-nanoparticles are $Pd^0$-nanoparticles.

7. The catalyst of claim 1, wherein a portion of the Pd-nanoparticles are in a $Pd_yM_x$ phase, wherein M is Zn or Zn and Al and optionally Cr, Mn, Cu and/or Mg, and wherein the $Pd_yM_x$ phase is formed through activation in a hydrogen atmosphere.

8. The catalyst of claim 1, wherein the Pd-nanoparticles have a size of between 0.5 and 100 nm.

9. The catalyst of claim 1, containing between 0.001 and 5 wt.-% of Pd nanoparticles.

10. The catalyst of claim 1, containing between 0.01 and 20 wt.-% of ZnO and/or MgO and optionally Cr, Mn, Cu and/or Al, based on the weight of the catalyst.

11. A process of reacting an organic starting material with hydrogen in the presence of the catalyst of claim 1.

12. The process of claim 11, wherein the organic starting material comprises a carbon-carbon triple bond.

13. The process of claim 11, wherein the organic starting material is an alkynol.

14. The process of claim 11, wherein the organic starting material is a compound of formula (I)

(I)

wherein $R_1$ is H, a linear or branched $C_5$-$C_{35}$ alkyl moiety or a linear or branched $C_5$-$C_{35}$ alkenyl moiety, wherein the C chain can be substituted, and $R_2$ is linear or branched $C_1$-$C_4$ alkyl, wherein the C chain can be substituted.

15. The process of claim 14, wherein $R_1$ is H, a linear or branched $C_5$-$C_{30}$ alkyl moiety or a linear or branched $C_5$-$C_{30}$ alkenyl moiety, wherein the C chain can be substituted, and $R_2$ is a linear or branched $C_1$-$C_4$ alkyl moiety, wherein the C chain can be substituted.

16. The process of claim 14, wherein $R_1$ is H, a linear or branched $C_6$-$C_{16}$ alkyl moiety or a linear or branched $C_6$-$C_{16}$ alkenyl moiety, wherein the C chain can be substituted, and $R_2$ is a $C_1$-$C_2$ alkyl moiety, wherein the C chain can be substituted.

17. The process of claim 14, wherein $R_1$ is a linear or branched $C_6$-, $C_{11}$- or $C_{16}$- alkyl moiety or a linear or branched $C_6$-, $C_{11}$- or $C_{16}$-alkenyl moiety, and $R_2$ is a $C_1$-$C_2$ alkyl moiety.

18. The process of claim 14, wherein the organic starting material is chosen from the group consisting of 2-methyl-3-butyn-2-ol (MBY) and dehydroisophytol (DIP).

19. The process of claim 11, wherein the process of reacting the organic starting material with hydrogen occurs at a pressure which is between 1.1 and 30 bar.

20. The process of claim 11, wherein the process of reacting the organic starting material with hydrogen occurs at a reaction temperature which is between 250 K and 420 K.

21. The process of claim 11, further comprising adding to the reaction at least one organic base selected from the group consisting of 3,6-dithia-1,8-octandiol, thiophene, di propyl sulfide, tetrahydrothiophene, quinoline, pyridine and diethylaminoethanol.

* * * * *